(12) United States Patent
Allen et al.

(10) Patent No.: US 6,610,874 B2
(45) Date of Patent: Aug. 26, 2003

(54) PROCESSES AND COMPOSITIONS FOR THE PRODUCTION OF CHIRAL AMINO-NITRILES

(75) Inventors: David Robert Allen, LaGrange Park, IL (US); Crystal A. Achenbach-McCarthy, Lombard, IL (US)

(73) Assignee: PCBU Services, Inc., Wilmington, DE (US)

( * ) Notice: Subject to any disclaimer, the term of this patent is extended or adjusted under 35 U.S.C. 154(b) by 0 days.

(21) Appl. No.: 09/967,270

(22) Filed: Sep. 28, 2001

(65) Prior Publication Data

US 2003/0065207 A1 Apr. 3, 2003

(51) Int. Cl.$^7$ .............................................. C07C 253/16
(52) U.S. Cl. ....................... 558/316; 558/311; 558/332; 564/215
(58) Field of Search ................................. 558/311, 316, 558/332; 564/215

(56) References Cited

FOREIGN PATENT DOCUMENTS

| JP | 2001002630 | 1/2001 |
|---|---|---|
| WO | WO 94/00095 | 1/1994 |

OTHER PUBLICATIONS

Database CASREACT on STN, 121:280227, Constantinou–Kokotou et al., 'Synthesis of 1,3–diamines.' Org. Prep. Preced. Int. (1994), 26(5), p. 599–602 (reaction abstract).*
Database CAPLUS on STN, Acc. No. 1994:680227, Constantinou–Kokotou et al., 'Synthesis of 1,3–diamines.' Org. Prep. Preced. Int. (1994), 26(5), p. 599–602 (abstract).*
Database CASREACT on STN, 131:5492, Kokotos et al., 'Synthetic routes to lipidic diamines and amino alcohols: a class of potential antiinflammatory agents.' Lipids (1999), 34 (3), p. 307–311 (reaction abstract).*
Database CAPLUS on STN, Acc. No. 1999:243656, Kokotos et al., 'Synthetic routes to lipidic diamines and amino alcohols: a class of potential antiinflammatory agents.' Lipids (1999), 34 (3), p. 307–311 (abstract).*
"Synthesis of homochiral N–Boc–B–aminoioaldehydes from N–Boc–B–aminonitriles", Bull Soc Chim Fr (1997), 134, 713–717.
"A Facile Synthesis of Methanesulfonate Esters", The Journal of Organic Chemistry, vol. 35, No. 9, (1970) pp 3195–3196.
"(S)–Pyroglutamic Acid, (S)–Malic Acid, and (S)–Serine as Useful Starting Materials in the Synthesis of Enantiopure Hydroxyamidines", European Journal of Organic Chemistry, No. 1 (2000), pp. 115–124.
"Synthesis of Enantiopure N–and C–Protected homo–B–Amino Acids by Direct Homologation of a–Amino Acids", Tetrahedron, vol. 51 51., No. 45 (1995) pp. 12337–12350.
Constantinou–Kokotou et al., "Synthesis if 1,3–Diamines", Org. Prep. Preced. Int. vol. 26, No. 5. pp 599–602 (1994).
Kokotos et al., "Synthesis Routes to Lipidic Diamines and Amino Alcohols: A Class of Potential Antiinflammatory Agents", Lipids vol. 34, No. 3, pp 307–311 (1999).
"Synthesis of homochiral N–Boc–B–aminioaldehydes from N–boc–B–aminonitriles", Bull Soc Chim Fr (1997), 134, 713–717.
"Synthesis of Enantiopure N–and C–Protected homo–B–Amino Acids by Direct Homologation of a–Amino Acids", Tetrahedron, vol. 51, No. 45 (1995) pp. 12337–12350.
Copy of International Search Report completed on Dec. 20, 2002.

\* cited by examiner

*Primary Examiner*—Brian Davis
(74) *Attorney, Agent, or Firm*—Baker & Daniels

(57) ABSTRACT

Processes for the efficient production of chiral amino nitrites are disclosed. Generally, the processes include the esterification of the alcohol of a amino protected alcohol followed by nucleophilic substitution of the ester with a cyano group. In an exemplary embodiment the chiral amino nitrile produced is (R)-3-aminopentanenitrile.

15 Claims, 6 Drawing Sheets

PROCESSES AND COMPOSITIONS FOR THE PRODUCTION OF CHIRAL AMINO-NITRILES

BACKGROUND OF THE INVENTION

Amino nitrites, organic compounds having at least one amino group and at least one nitrile group, have been found to be useful starting materials and intermediates in the production of fine chemicals. For example, (R)-3-aminopentanenitrile is particularly useful in the synthesis of a cholesterol reducing agent. The state of the art for producing these compounds utilizes a phase transfer cyanide source or displaces the iodine of an intermediate iodo compound. Unfortunately, this methodology has proven to be infeasible on an industrial scale.

One route for the production of amino nitrites is disclosed in Caputo et al, Synthesis of Enantiopure N- and C-Protected homo-β-Amino Acids by Direct Homologation of the α-Amino Acids, Tetrahedron Letters, Vol. 51, No. 45, pp. 123337–12350, 1995. Caputo discloses the use of a triarylphosphine-iodine polymer bound complex in the presence of imidazole to replace the hydroxyl group with the iodo group and the subsequent displacement of the iodo group with a cyanide. The introduction of polymer bound reactants makes this methodology costly and undesirable. Moreover, Caputo utilized tetraethylammonium cyanide as a nucleophilic reagent and experienced significant deprotection of the amino group.

Another reaction scheme disclosed in Toujas, et al., Synthesis of homochiral N-Boc-β-aminoaldehydes from N-Boc-β-aminonitriles, Bull. Soc. Chim. Fr. (1997), 134(7), 713–717 utilizes costly solvents and results in low yields. Toujas, et al., discloses the N-Boc protection of the amino group and mesylation of the hydroxyl with methanesulfonyl chloride in the presence of triethylamine at room temperature. According to Toujas, et al., nucleophilic substitution with sodium cyanide in DMSO gives a relatively low yield of 56%.

What is needed is a reaction scheme for the production of amino nitrites from amino alcohols that is industrially feasible. Specifically what is needed is a reaction scheme that provides high yields while utilizing inexpensive reagents.

SUMMARY OF THE INVENTION

In one embodiment of the present invention a process for the preparation of chiral amino nitrile compounds from chiral amino alcohols is provided. In one aspect the process esterifies a chiral amino alcohol having an alcohol group and a protected amine group to create an electrophilic carbon having a leaving group and subsequently substitutes a cyanide for the leaving group in the presence of dimethylformamide to form a chiral amino nitrile having a protected amine group. In another aspect of the present invention the protecting group of the amine comprises t-butoxy carbonyl.

In a particularly useful embodiment the esterification of the hydroxyl is performed using a sulfonyl chloride and the leaving group comprises a sulfonate. In a preferred embodiment the esterification is performed using methyl sulfonyl chloride and the leaving group is methyl sulfonate.

In still another embodiment the cyanide used as a nucleophile is added as a salt. In a preferred embodiment sodium cyanide provided with an organic solvent is used as the nucleophile.

Another embodiment of the present invention provides for the additional step of removing the protecting group from the protected amine of the chiral amino nitrile. In one aspect of the present process the protecting group is removed by addition of an acid. In a preferred embodiment methyl sulfonic acid is used to remove the protecting group. In still another embodiment the protecting group is removed in the presence of an organic solvent.

Other objects and further benefits of the present invention will become apparent to persons having ordinary skill in the art from the following written description and accompanying figures.

DESCRIPTION OF THE PREFERRED EMBODIMENTS

Figure 1:
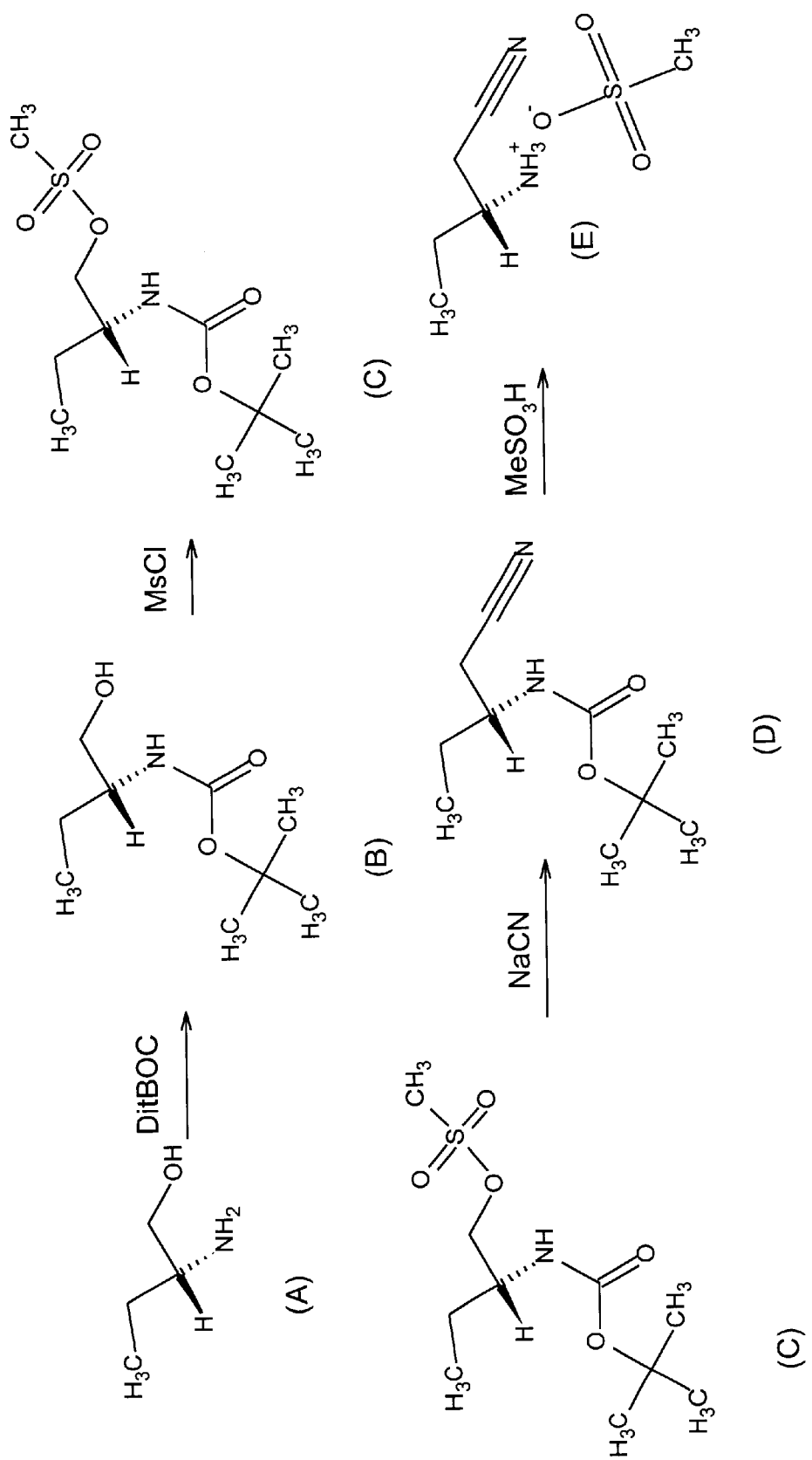
FIG. 1 Production of Chiral Amino Nitrile According to One Embodiment of the Present Invention.

For the purposes of promoting an understanding of the principles of the invention, reference will now be made to the embodiments illustrated in the drawings and the examples and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides a process and an intermediate useful in the preparation of amino nitrites. In one embodiment, a process is provided for the preparation of chiral amino nitrites from chiral amino alcohols. Generally, the present invention involves protecting the amino group of a chiral amino alcohol and esterifying the alcohol group of the protected chiral amino alcohol to create an electrophilic carbon having a leaving group. Next, a cyanide replaces the leaving group to form a chiral amino nitrile having a protected amino group. Thereafter the protecting group is removed from the protected amino group to form a chiral amino nitrile.

Referring now to FIG. 1, one embodiment of the overall reaction scheme just described will be discussed. As depicted in FIG. 1, compound (A) is the chiral compound 2-amino-1-butanol. Chiral as used herein refers to compounds having stereoisomers wherein each stereoisomer has a mirror image that cannot be super imposed over the original stereoisomer. Compound (A) of FIG. 1 has two stereo enantiomers, with a chiral carbon atom located at the 2 position of the butanol backbone. Chiral carbon atoms can be characterized as those carbon atoms that are bonded to four different groups, as depicted here in FIG. 1,(A). This chiral or stereochemical conformation is important in many compounds but is specifically important in compounds that are to be used as pharmaceutical or therapeutic agents.

The chiral amino alcohol utilized as the starting material of the present invention in one embodiment is 2-amino-1- butanol. It has been determined that other amino alcohols can be utilized as the starting material. It is generally accepted that starting compounds in reaction processes having reactive groups proximate to one another lead to unwanted side reactants upon reaction. Because the present invention exemplifies the use of an amino nitrile having a reactive hydroxyl proximate to the reactive amino, other amino alcohols with these reactive groups less proximate to one another can be processed equally as well according to the present invention.

In one embodiment, a protecting group is bonded to the amino group of the chiral amino alcohol. It is well known in the art that organic functional groups having lone pairs of electrons are particularly reactive with certain chemical reagents. Amines and hydroxyl groups are examples of reactive groups having lone pairs of electrons. In one aspect of this invention it is necessary to protect the amine group from reacting with selected reagents slated for reaction with the hydroxyl group. By protecting the amine, side reactions with other reagents are avoided. Once the selected reaction takes place the protecting group can be removed for example by hydrogenolysis, or acidolysis.

In a particular embodiment the protecting group of the amine is t-butoxy carbonyl (t-BOC). It has been determined that the amine group can be protected by combining the amino alcohol with di-t-butyldicarbonate (DiBOC) under neutral or basic conditions. After the reaction is complete the protected amino alcohol can be readily retrieved from the reaction mixture, according to accepted reaction mixture clean-up procedures. It has been concluded that the usual alkoxycarbonyl N-protecting groups currently utilized in peptide chemistry, namely, such as N-Cbz (benzyloxycarbonyl) and the like can be utilized as well.

In one aspect these protective groups play a passive role in synthetic processes. However, each operation of introduction and removal of a protective group adds a step to the synthetic sequence and it is desirable to minimize the number of such operations. In the present invention, primary and secondary amino groups are nucleophilic and easily oxidized. Because of this nucleophilicity the amino reactivity may lead to side reactions. To limit such side reactions, the amino group is protected. Generally, the nucleophilicity of this group can be masked by isolation. In one embodiment of the present invention the protected amino butanol is t-butoxycarbonyl (2R)-amino-1-butanol (BOC-ABA), shown as compound (B) in FIG. 1. Carbamates including carbobenzyloxy groups are particularly useful. The benzyl C—O bond of the carbamate can easily be hydrogenolized to regenerate the amine. The protecting group of the amine can be any protecting group that masks the nucleophilicity of the amine thereby prohibiting cross and side reactions.

According to another embodiment of the present invention, once protected, the alcohol of the protected compound can be esterified. Tosyl chlorides have been found to be particularly useful for esterifying the alcohol of the protected amino alcohol. Upon formation, the sulfate ester is an excellent leaving group from the electrophylic carbon to which it is attached. Good leaving groups are electron withdrawing and create a partial positive charge on the adjacent carbon atom. This slightly positive charge causes the carbon atom to become electrophilic. According to general lewis acid/base principals, electrophilic carbons readily accept negatively charged compounds or elements such as nucleophiles.

In a particular embodiment of the present invention methyl sulfonyl chloride is reacted with the alcohol of the amino protected compound to form the amino methyl sulfonate, methanesulfonate-N-t-butoxycarbonyl-(2R)-amino-1-butanol (BOC-ABA-OMs), shown as compound (C) in FIG. 1. In one aspect, under neutral or basic conditions the methyl sulfonyl chloride is combined with the alcohol at a relatively low temperature, after complete addition of the reagents, the reaction mixture is stirred for several hours until the amino protected ester is formed. To retrieve the amino protected ester from the reaction mixture, the reaction mixture can be diluted with an acid and washed with water and subsequently crystallized to obtain the amino protected ester.

The above described amino protected ester is an excellent intermediate for the production of chiral amino nitrites. In one embodiment, this intermediate is characterized by an electrophylic carbon beta to the carbon having the amino group protected. It has been concluded that the leaving group of the electrophylic carbon may be any leaving group that will allow for the efficient addition of the cyano group to the carbon. These leaving groups include, but are not limited to, sulfonates, either methyl or phenyl and the like.

One embodiment of the present invention includes substituting a cyanide for the leaving group of the electrophylic carbon in the presence of dimethylformamide (DMF) to form high yields of chiral amino nitrile having a protected amino group. The DMF used to perform this reaction can be of reagent grade. Herein, substituting refers to a nucleophilic substitution. As mentioned earlier the leaving group has an electron withdrawing effect on the carbon to which it is attached, thereby making the carbon electrophylic. According to the present invention cyanide is combined with the protected amino compound to form a nitrile compound. In still another embodiment of the present invention the cyanide is added as a sodium salt to the protected amino compound in the presence of a neutral or basic solution. It is contemplated that potassium cyanide will sufficiently perform this function as well. It is further contemplated that this reaction is to be performed at room temperature or slightly above. Upon completion of the reaction, the reaction mixture can be analyzed by NMR or chromatography to verify the completion of the reaction prior to product purification. Thin layer chromatography can be efficiently used to monitor the present reaction.

Upon reaction completion the product can be isolated with a water wash, wherein the water may have a significant ionic content. After the wash, the organics can be reduced to a thin oil to which alcohol and water are added and the resulting compound can be subsequently crystallized (seeded if necessary). In an exemplary embodiment, the procedure above was utilized to produce the chiral amino nitrile compound N-t-butoxycarbonyl-(3R)-aminopentanenitrile (BOC-APN) which is depicted as compound (D) in FIG. 1. Particularly useful in thin layer chromatography monitoring of the reaction mixture is the use of phosphomolybdic acid (PMA). When applied prior to heating a prepared thin layer chromatography plate, once heated, the BOC-ABA-OMs starting materials display a dark spot and the BOC-APN display a lighter yellow spot.

As alluded to earlier the protected amino nitrile can be deprotected by acidolysis. In a particularly useful embodiment the acidic compound can be methyl sulfonic acid, which by design can be generated as the sulfonate salt by-product of the nitrile production described previous. In a particular aspect of this invention the deprotecting solvent is an organic solvent. In a preferred embodiment the organic solvent is a combination of acetonitrile and ethyl acetate. Reagent grade solvents have been found to perform sufficiently. Upon acidolysis with methyl sulfonic acid the methyl sulfonic acid salt of the amino nitrile is prepared. In a particular embodiment this compound is (R)-3-aminopentanenitrile methanesulfonic acid salt (APN-MsOH), depicted as compound (E) in FIG. 1. Acidolysis can be performed in a reaction vessel at room temperature or above. Upon reaction completion the solids can be recovered by simply cooling the reaction mixture to room temperature and subsequent removal by filtration. The filtered solids can be characterized as the reaction product by NMR and/or HPLC methodology. Once produced these compounds can be easily utilized as precursors for pharmaceutically valuable compounds.

The following non-limiting examples further demonstrate the present invention.

EXAMPLE 1

Preparation of Methanesulfonate-N-t-butoxycarbonyl-(2R)-amino-1-butanol (BOC-ABA-OMs) from 2-amino-1-butanol

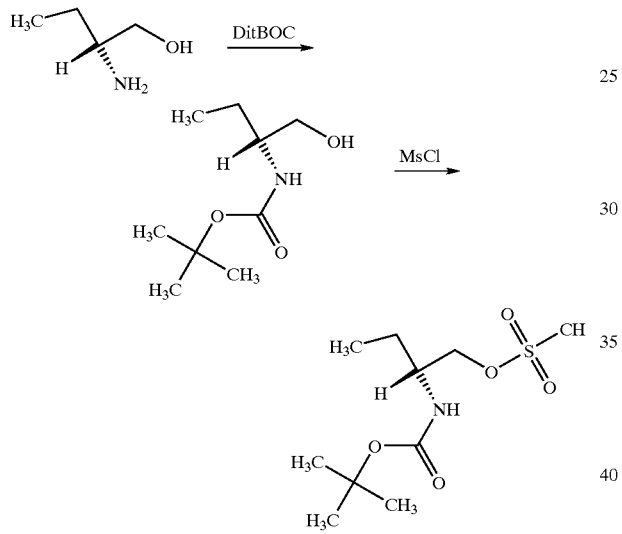

L-(−)-2-amino-1-butanol (50 g, 0.561 mol) was charged to a reaction vessel immediately followed by toluene (400 mL). To this solution was added triethylamine (82 mL, 59.5 g, 0.588 mol, 1.05 eq). DiBOC (128.5 g, 0.589 mol, 1.05 eq) in toluene (50 mL) was added to the reaction vessel dropwise keeping the reaction temperature below 30° C. After complete addition of the DIBOC, the reaction mixture was allowed to come to room temperature and stirred for 3–4 hours.

$CO_2$ was removed from the reaction vessel in vacuo at 25–30° C. for 15 minutes. The solution was treated with additional triethylamine (20 mL, 14.52 g, 0.143 mol, 0.26 eq) and diluted with tolulene (100 mL) and ethyl acetate (300 mL). The mixture was cooled to 0° C. and methanesulfonyl chloride (52 mL, 76.96 g, 0.672 mol, 1.2 eq) was added dropwise to the reaction vessel keeping the reaction temperature below 10° C. After complete addition the mixture was allowed to warm to room temperature and stirred for 4–5 hours.

To isolate the reaction product, the mixture was diluted with 1 N HCl (300 mL) to form a two phase solution having an aqueous and an organic phase. The organic phase was separated from the aqeous phase, collected and washed with water (300 mL). The organics were again separated from the aqueous phase and diluted with heptane (1 L). To induce crystallization the solution was cooled to 10° C. with stirring for 1.5 to 2 hours. The resulting solids were collected by filtration, washed with heptane (2×150 mL) and dried in vacuo at room temperature.

The recovered solid material was characterized using a Brüker Avance™ 400 mHz Digital NMR. The results are as follows: $CDCl_3 \delta = 0.91$ (t, 3H), 1.38 (s, 9H), 1.47–1.57 (m, 2H), 2.96 (s, 3H), 3.68 (br s, 1H), 4.14–4.15 (d, 2H), 4.54 (s, 1H). The material was further characterized by gas chromatography and the resulting chromatogram is demonstrated in FIG. 2.

Figure 2:
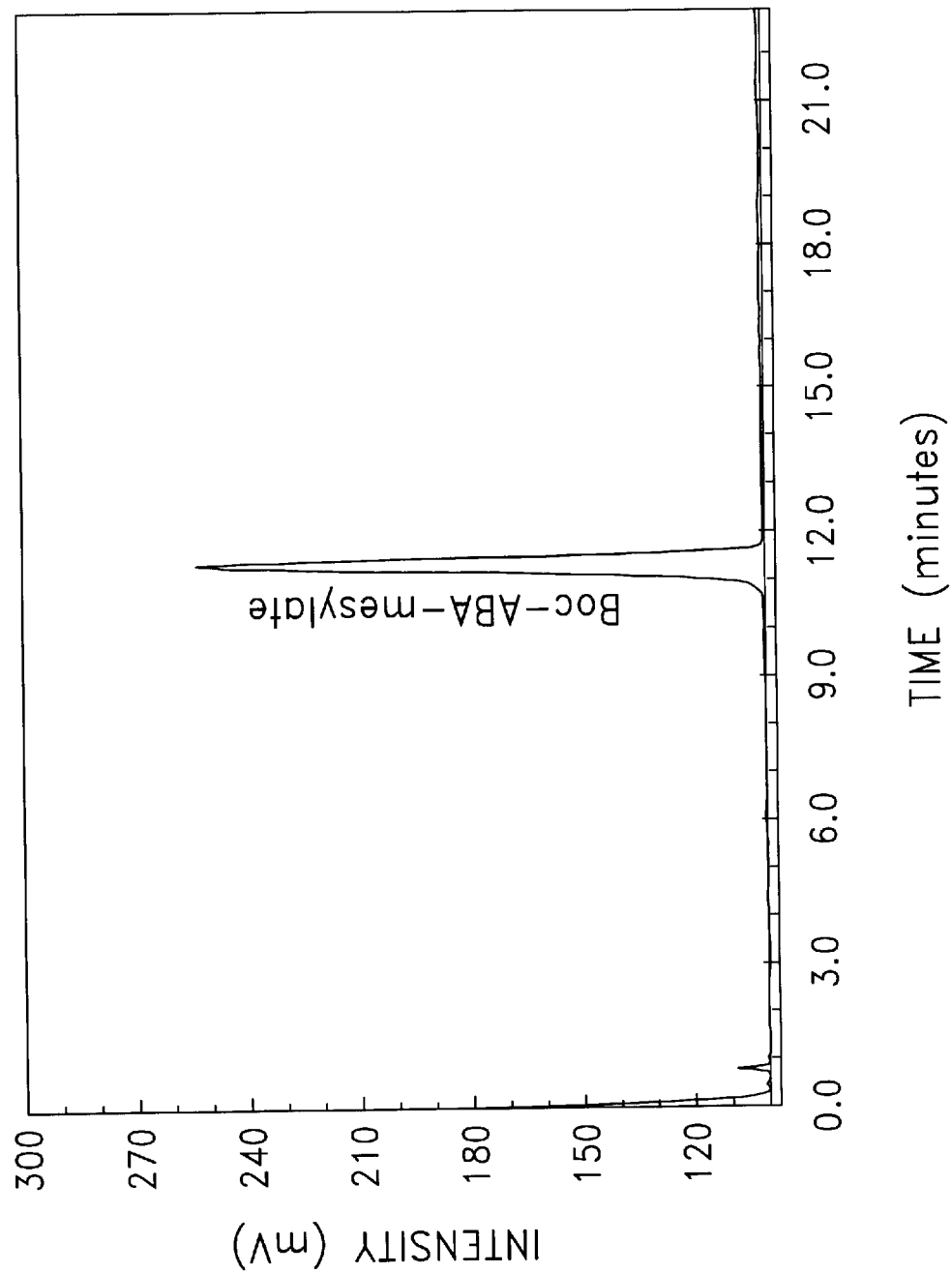
FIG. 2 Gas Chromatogram of BOC-ABA-OMs produced according to the present invention.

As the chromatogram in FIG. 2 and the NMR demonstrates the 2-amino-1-butanol was efficiently protected and esterified. The reaction had a yield of approximately 80%.

EXAMPLE 2

Preparation of N-t-butoxycarbonyl-(3R)-aminopentanenitrile (BOC-APN) from BOC-ABA-OMs

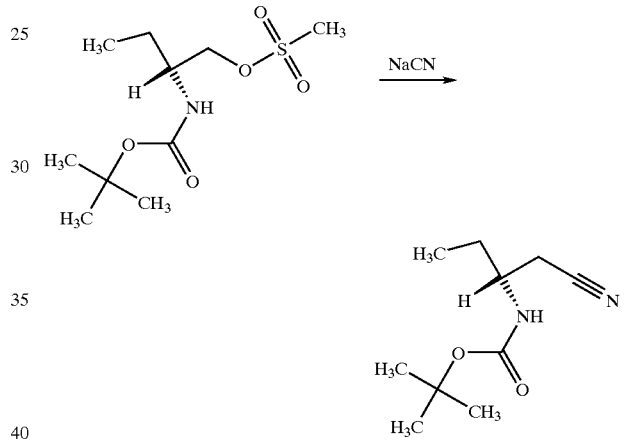

BOC-ABA-OMs (40 g, 0.15 mol) was charged to a reaction vessel. To this was added dimethylformamide (DMF, 250 mL) and sodium cyanide (9.56 g, 0.195 mol, 1.3 eq). The reaction mixture was heated to 50° C. and stirred for 11 to 18 hours. The reaction was checked by TLC to verify completion prior to workup. SilicaGel® 60 $F_{254}$ thin layer chromatography plates were spotted with reaction mixture and run in 2:1 EtOAc/Hexane mobile phase. The TLC plate was dipped in a 5% (wt/wt) solution of phosphomolybdic acid in ethanol. The TLC plate was subsequently heated to 100° C. The BOC-ABA-OMs starting material showed as a dark spot, and the BOC-APN showed as a lighter yellow spot.

After the reaction was complete the mixture was cooled to room temperature, ethyl acetate (200 mL) and water (150 mL) were added to the reaction mixture thereby forming two liquid phases. The organic layer was separated and washed with water (2×200 mL) and with brine (1×200 mL). The solvents were removed in vacuo to reveal a thin oil. To this oil was added methanol (60 mL) and water (130 mL). The mixture was cooled to −5° C. and stirred overnight at −5° C. to complete crystallization (crystallization began within 1.5 hours of seeding). The washed solids were collected by filtration and washed twice with water (2×100–150 mL). Solids were dried in vacuo at room temperature overnight.

The solids were then characterized by melting point using a Thomas Hoover uni-melt capillary melting point apparatus. The melting point was found to be 59–63° C. The solids were then characterized using a Brüker Avance™ 400 mHz Digital NMR. The carbon and proton NMR results were as follows: $^1$H NMR (400 MHz), CDCl$_3$ δ=0.94 (t, 3H), 1.4 (s, 9H), 1.55–1.65 (m, 2H), 2.4–2.5 (dd, 1 H), 2.6–2.7 (dd, 1 H), 3.65 (m, 1H), 4.75 (d, 1 H) $^{13}$CNMR (100 MHz); δ=10.8, 23.8, 26.9, 28.7, 49.1, 80.4, 117.8, 155.6.

Figure 3:
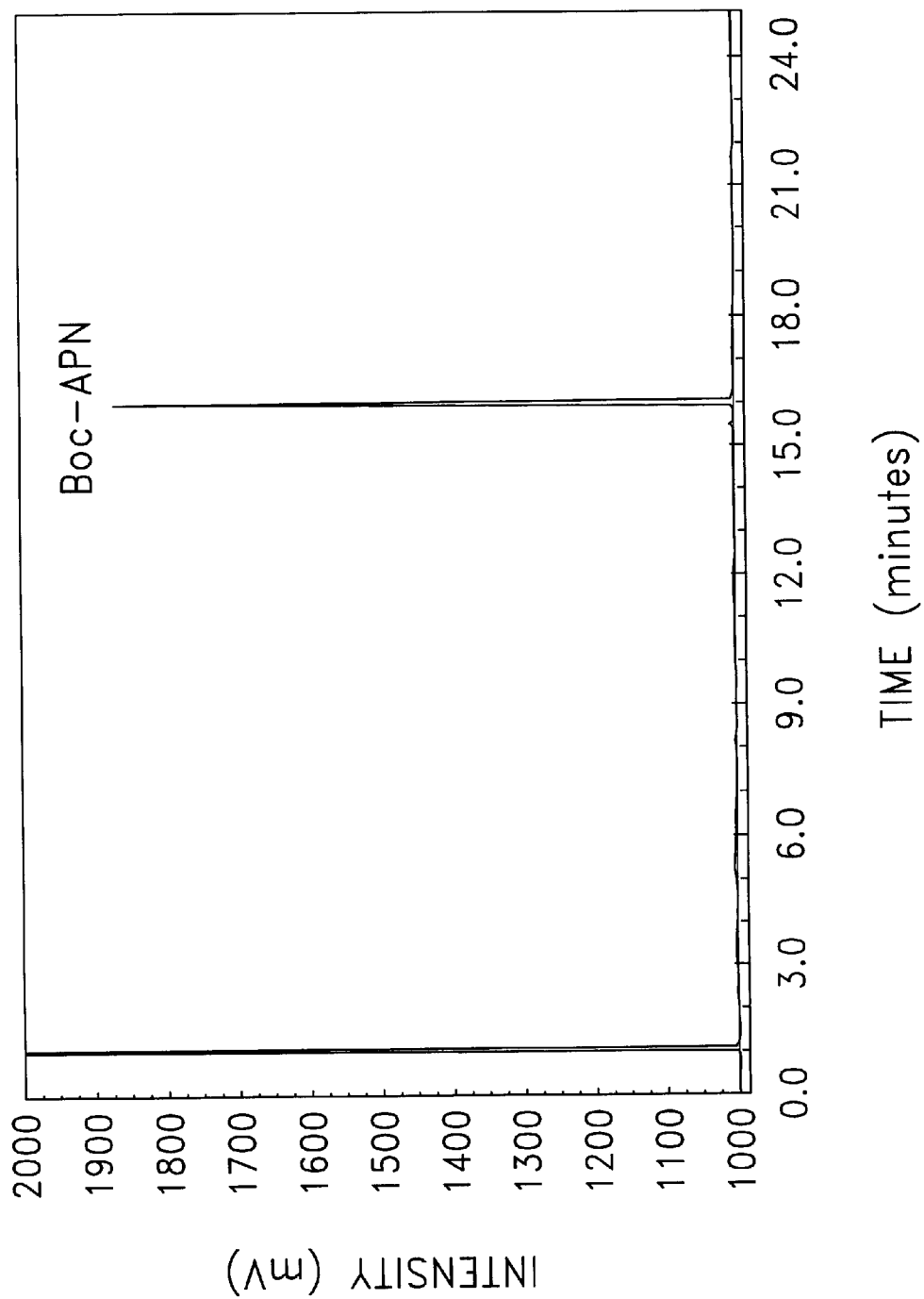
FIG. 3 Gas Chromatogram of BOC-APN produced according to the present invention.

The material was further characterized by gas chromatography and the resulting chromatogram is demonstrated in FIG. 3.

As the chromatogram in FIG. 3 and the NMR demonstrates the protected amino nitrile was efficiently protected and esterified. The reaction had a yield of approximately 64.4%.

EXAMPLE 3

Preparation of (R)-3-aminopentanenitrile methanesulfonic acid salt (APN-MsOH) from BOC-APN

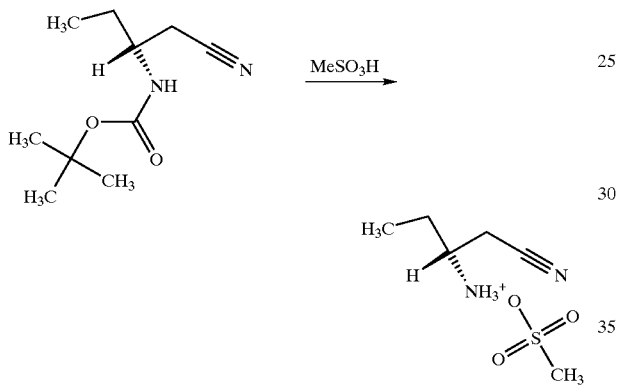

BOC-APN (10 g, 0.05 mol) was charged to a reaction vessel, followed by acetonitrile (25 mL), ethyl acetate (12.5 mL) and methanesulfonic acid (3.9 mL, 5.77 g, 0.06 mol, 1.2 eq). The reaction mixture was stirred at room temperature for approximately 30 minutes until solids formed. The reaction mixture was then heated to 65–70° C. and stirred until all solids dissolved—approximately 30–45 minutes. The reaction mixture was cooled slowly to room temperature and then to 5–10° C. Solids were collected by filtration and washed with acetonitrile (3×50 mL) and subsequently dried in vacuo at 40–45° C.

Material was characterized using a Brüker Avance™ 400 mHz Digital NMR: $^1$H NMR; DMSO δ=0.9 (t, 3H), 1.55–1.75 (m, 2H), 2.45 (s, 3H), 2.75–3.25 (ddd, 2H), 3.4 (m, 1H), 8.2 (br s, 2H); $^{13}$CNMR (100 MHz) δ=9.6, 20.7, 25.3, 48.4, 117.5.

The product was also analyzed according to chiral and achiral liquid chromatography techniques. In both instances Hewlett-Packard® high performance liquid chromatographs equipped with UV detectors were utilized. The results of the chiral analysis are shown in FIG. 4 and the results of the achiral analysis are shown in FIG. 5.

Figure 4:
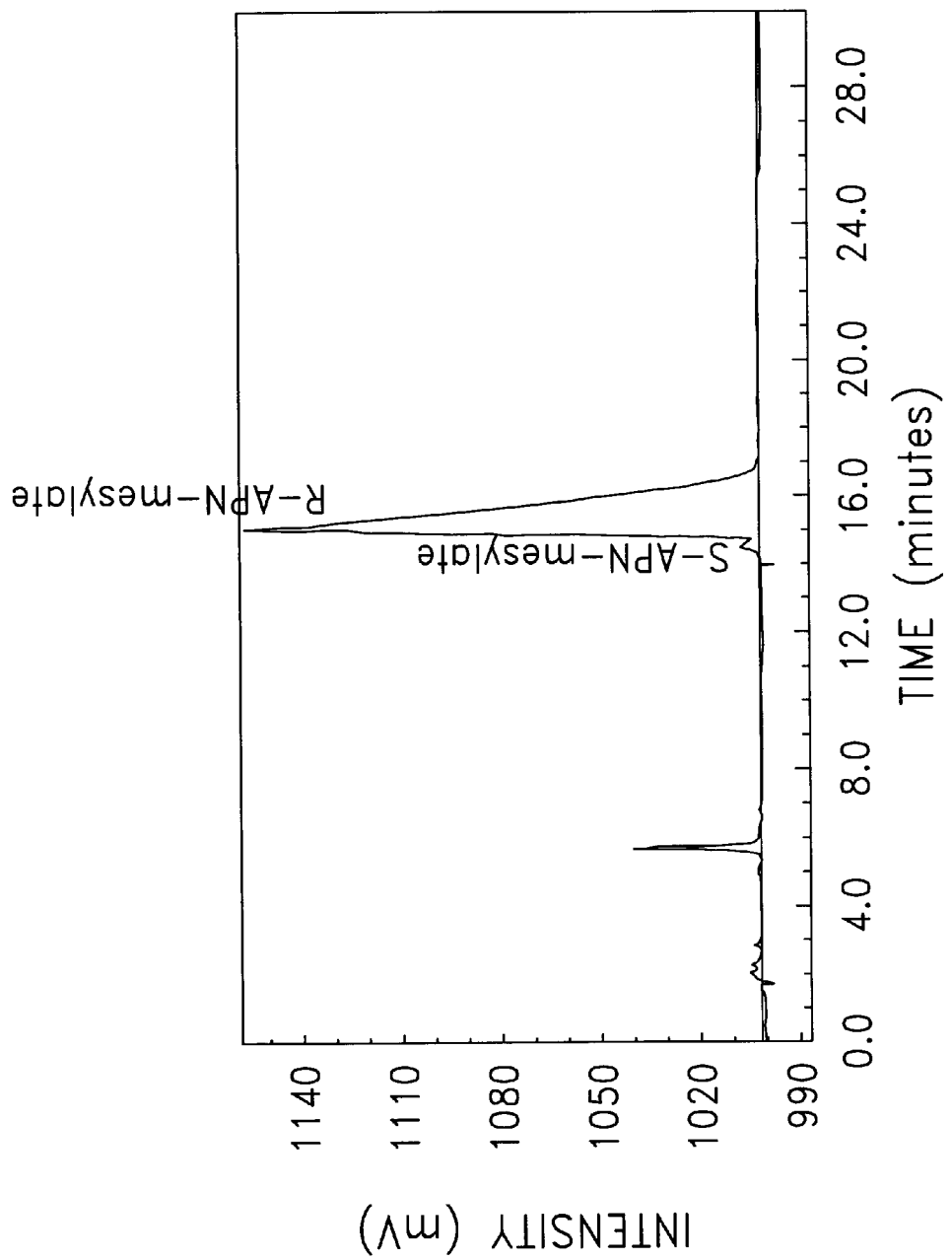
FIG. 4 Liquid Chromatogram (chiral) of APN-MsOH produced according to the present invention.
Figure 5:
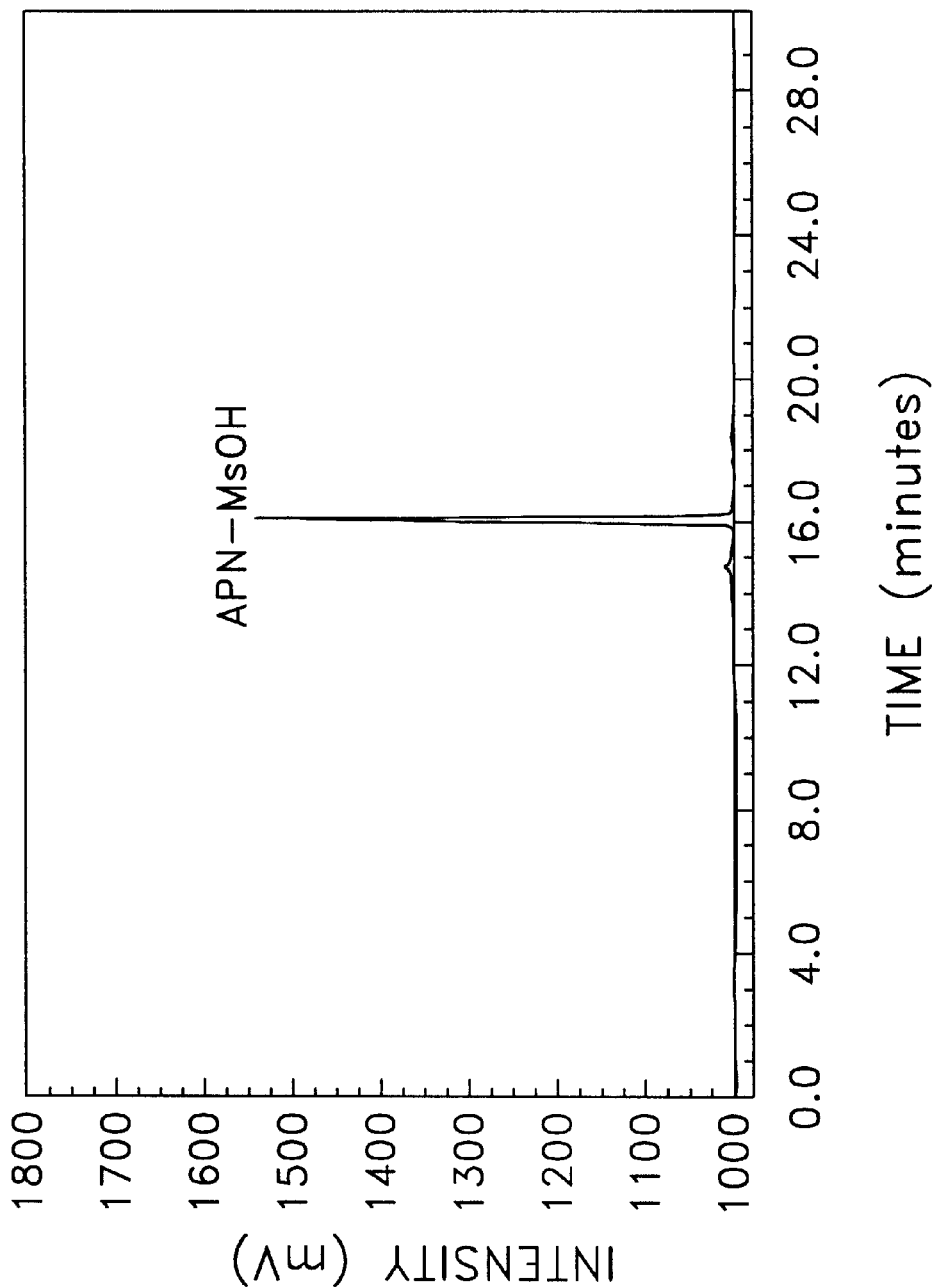
FIG. 5 Liquid Chromatogram (achiral) of APN-MsOH produced according to the present invention.
Figure 6:
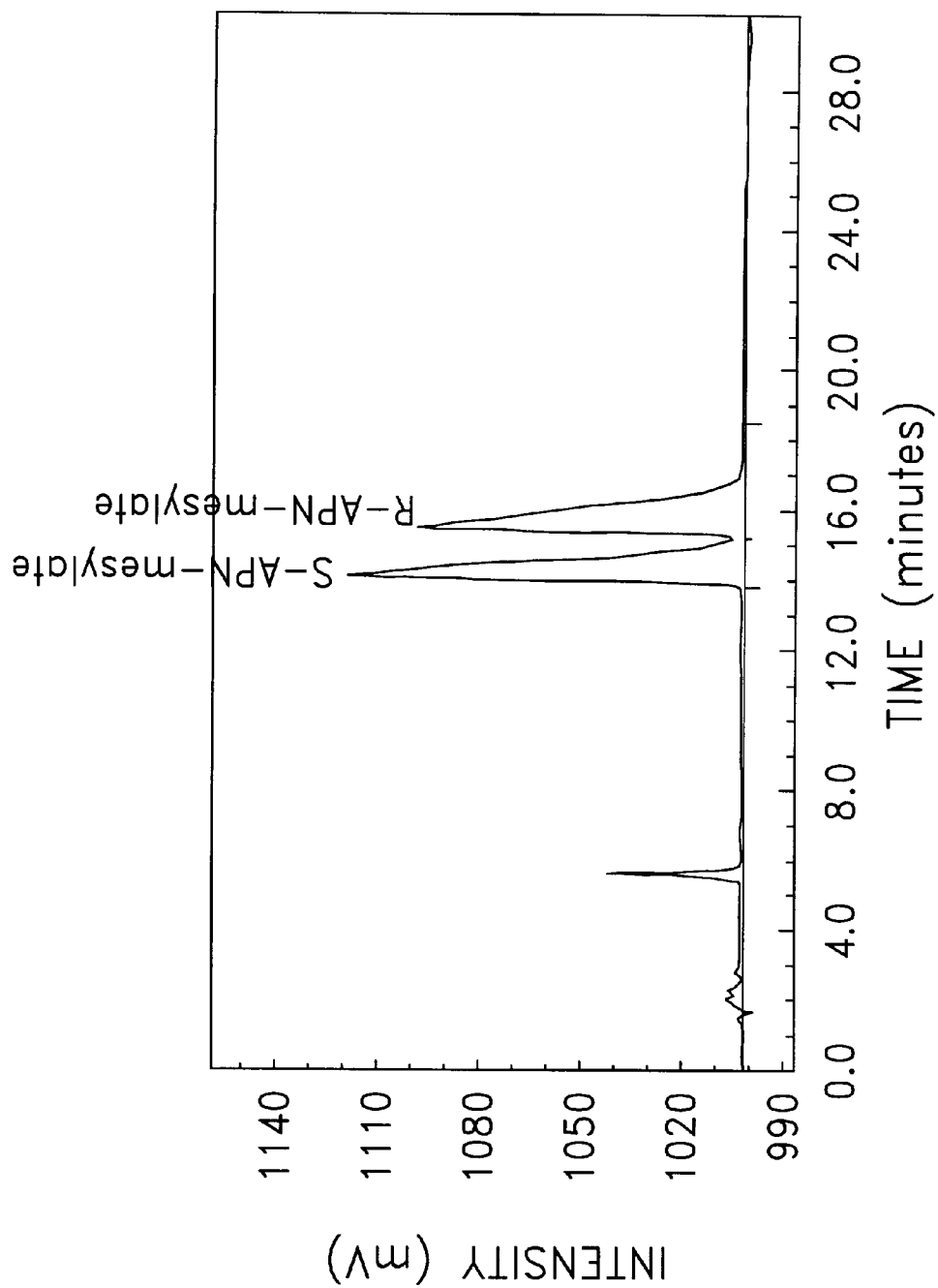
FIG. 6 Liquid Chromatogram (chiral) of racemic APN-MsOH.

As the NMR data and FIGS. 4 and 5 demonstrate, essentially enantiomerically pure amino-nitrile is produced according to the present invention. By comparison with the racemic mixture of FIG. 6, FIG. 4 demonstrates the enantiomerically pure product of the present invention While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A process for the preparation of chiral amino nitrile compounds from chiral amino alcohols comprising:
   a.) providing a chiral amino alcohol comprising

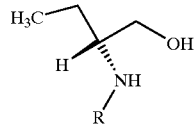

wherein R represents a protecting group;
   b.) esterifying the alcohol group to create an ester having an electrophilic carbon having a leaving group; and
   c.) substituting a cyanide for said leaving group in the presence of dimethylformamide to form a chiral amino nitrile having a protected amine group.

2. The process of claim 1 wherein the R comprises t-butoxy carbonyl.

3. The process of claim 1 wherein the esterification of step b is performed using a sulfonyl chloride and the leaving group comprises a sulfonate.

4. The process of claim 3 wherein the sulfonyl chloride comprises methyl sulfonyl chloride and the leaving group comprises methyl sulfonate.

5. The process of claim 4 wherein an ester product of step b comprises

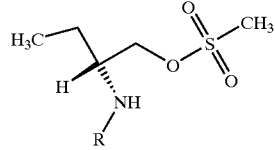

wherein R represents a protecting group.

6. The process of claim 1 wherein the cyanide is added as a salt.

7. The process of claim 6 wherein the salt comprises sodium cyanide.

8. The process of claim 1 wherein the chiral amino nitrile having a protected amine group comprises:

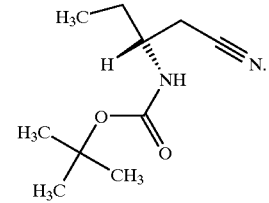

9. The process of claim 1 further comprising:
   the additional step of removing the protecting group from the protected amine of chiral amino nitrile to form a chiral amino nitrile.

10. The process of claim 9 wherein the protecting group is removed by addition of an acid.

11. The process of claim 10 wherein the acid comprises methyl sulfonic acid.

12. The process of claim 9 wherein the chiral amino nitrile has one chiral center.

13. The process of claim 12 wherein the chiral amino nitrile comprises:

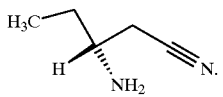

14. A process for the preparation of chiral amino nitrile compounds from chiral amino alcohols comprising:

a.) providing a chiral amino alcohol consisting essentially of:

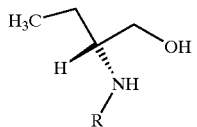

wherein R represents a protecting group;

b.) esterifying the alcohol group to create an ester having an electrophilic carbon having a leaving group; and c.) substituting a cyanide for said leaving group in the presence of dimethylformamide to form an essentially enantiomerically pure amino nitrile having a protected amine group.

15. The process of claim 14 further comprising the step of:

d) removing the protecting group from the protected amine of the essentially enantiomerically pure amino nitrile to form an essentially enantiomerically pure amino nitrile.

* * * * *